United States Patent  (10) Patent No.: US 8,538,700 B2
Badri et al.  (45) Date of Patent: Sep. 17, 2013

(54) METHOD OF DETERMINING SUBTERRANEAN FORMATION PARAMETERS

(75) Inventors: Mohammed Badri, Al-Khobar (SA); Patrice Ligneul, Al-Khobar (SA); Jean-Marc Donadille, Al-Khobar (SA)

(73) Assignee: Schlumberger Technology Corporation, Cambridge, MA (US)

( * ) Notice: Subject to any disclaimer, the term of this patent is extended or adjusted under 35 U.S.C. 154(b) by 497 days.

(21) Appl. No.: 12/835,388

(22) Filed: Jul. 13, 2010

(65) Prior Publication Data

US 2012/0011927 A1 Jan. 19, 2012

(51) Int. Cl.
*G01V 1/40* (2006.01)

(52) U.S. Cl.
USPC .......................................................... 702/7

(58) Field of Classification Search
USPC .......................................................... 702/7
See application file for complete search history.

(56) References Cited

U.S. PATENT DOCUMENTS

| | | | |
|---|---|---|---|
| 6,393,363 B1 | 5/2002 | Wilt et al. | |
| 6,765,380 B2 | 7/2004 | Freedman et al. | |
| 7,363,164 B2 | 4/2008 | Little et al. | |
| 7,532,983 B2 | 5/2009 | Montaron | |
| 8,005,619 B2 | 8/2011 | Akbar | |
| 2007/0112518 A1* | 5/2007 | Montaron | 702/1 |
| 2007/0276639 A1 | 11/2007 | Montaron et al. | |
| 2008/0290874 A1* | 11/2008 | Seleznev et al. | 324/337 |
| 2009/0259403 A1 | 10/2009 | Akbar | |
| 2010/0132448 A1* | 6/2010 | Donadille et al. | 73/152.08 |
| 2010/0198519 A1* | 8/2010 | Wilt et al. | 702/7 |

FOREIGN PATENT DOCUMENTS

| | | |
|---|---|---|
| WO | 0120366 A1 | 3/2001 |
| WO | 0120368 A1 | 3/2001 |

OTHER PUBLICATIONS

Wilt et al., "SPE 68802: Using Crosswell Electromagnetics to Map Water Saturation and Formation Structure at Lost Hills," SPE International, 2001: pp. 1-6.
Looyestijn et al., "Wettability-Index Determination by Nuclear Magnetic Resonance," SPE Reservoir Evaluation & Engineering, Apr. 2006, vol. 9(2): pp. 146-153.
Lloyestijn, "Wettability Index Determination from NMR Logs," SPWLA 48th Annual Logging Symposium, Jun. 2007: pp. 1-16.
Donaldson et al., "Relationship Between the Archie Saturation Exponent and Wettability," SPE Formation Evaluation, Sep. 1989: pp. 359-362.
Morrow, "Capillary Pressure Correlations for Uniformly Wetted Porous Media," The Journal of Canadian Petroleum, Oct.-Dec. 1976, vol. 15(4): pp. 49-69.
Wilt et al., "Crosshole Electromagnetic Tomography: A New Technology for Oil Field Characterization," The Leading Edge, Mar. 1995: pp. 173-177.
Wilt et al., "Crosswell Electromagnetic Tomography: System Design Considerations and Field Results," Geophysics, May-Jun. 1995, vol. 60(3): pp. 871-885.
Sweeney et al., "The Electrical Resistivity of Preferentially Water-Wet and Preferentially Oil-Wet Carbonate Rock," Producers Monthly, May 1960, vol. 24(7): pp. 29-32.

\* cited by examiner

*Primary Examiner* — Aditya Bhat
(74) *Attorney, Agent, or Firm* — Bridget Laffey; Rachel E. Greene; Jakub Michna

(57) ABSTRACT

A method for assigning a wettability or related parameter to a subvolume of formation located between two or more boreholes is described. The method includes the steps of obtaining measurements of resistivity at a subvolume, obtaining further parameters determining a relation between resistivity and saturation from logging measurements along the two or more boreholes, obtaining geological measurements defining geological or rock-type boundaries within the formation between the two or more boreholes, selecting the subvolume such that it is intersected by the geological or rock-type boundaries; transforming the resistivity measurements into the saturation at the subvolume; and using the saturation and/or the further parameters to determine the wettability or related parameter for the subvolume.

9 Claims, 2 Drawing Sheets

METHOD OF DETERMINING SUBTERRANEAN FORMATION PARAMETERS

FIELD OF THE INVENTION

This invention relates to methods of determining saturation, wettability or related attributes of subterranean formations, particularly of sections of the formation between two or more boreholes.

BACKGROUND

In oil exploration and production, the saturations and wettability of the rock/fluid system are major factors controlling the location, flow, and distribution of immiscible fluid phases in a reservoir. Saturations are relative measures of the fluid content in the formation pore space and, in the case of irreducible saturations, of the immobile or trapped fluid content. Together with wettability, saturations and irreducible saturations will determine the mobile and hence producible oil content of a reservoir.

In a porous medium of uniform wettability containing at least two immiscible fluids one of them is defined as the wetting fluid. At equilibrium, the wetting fluid occupies completely the smallest pores and is in contact with a majority of the rock surface (assuming, of course, that the saturation of the wetting fluid is sufficiently high). The non-wetting fluid occupies the center of the larger pores and form globules that extend over several pores.

The wettability of a three phase system of solid surface (s), oil (o) and water (w) is typically measured through the contact angle $\cos\theta$, which results from the equilibrium condition for the surface tensions at a point where the three phases meet:

$$\gamma_{so} - \gamma_{sw} - \gamma_{ow}\cos\theta = 0, \qquad [1]$$

where the surface tensions $\gamma$ have subscripts referring to the respective two phases forming the interface.

Methods of measuring wettability are described for example in the U.S. Pat. No. 7,532,983 to B. Montaron.

At the present state of art, macroscopic manifestation of wettability are used in the form of capillary pressure curve and relative permeability for the purpose of determining or simulating the production performance of a reservoir. Examples of such uses of the derivatives of wettability are described in the published United States Patent Application 2007/0276639 A and other published sources. Explicit maps of fields of a wettability parameter are therefore typically not included into reservoir simulations as the dependence of fluid movement on wettability is implicit and arises out of capillary pressure and relative permeability. Therefore it should be understood that, depending on the context, reference to wettability in this description may include reference to such closely related parameters. In general the industry is currently more concerned with developing databases linking core capillary pressure and relative permeability measurements at various wettability states to rock types. The latter are often characterized by a standard wettability index (Amott, Amott-Harvey, USBM) instead of contact angles. However the various indices and contact angle are equivalent.

The so-called wettability index measurements on cores can be used to map the patterns of rock wettability variation across the reservoir and by rock type. Given the wettability index and rock type at any point in the reservoir, a set of capillary pressure Pc and relative permeability curves Kr can be assigned in a reservoir simulator such as Schlumberger's Eclipse™ for every spatial location using for example an average Pc calculated by $$P_c = \frac{\gamma_{ow}\cos\theta}{2\pi r} \qquad [2]$$

where r represents an effective capillary or pore radius for the formation.

Given the generally very sparse availability of detailed core analysis measurements however, sets of Pc and Kr curves are more often assigned solely by rock type with little regard to the variation of wettability across the reservoir for the same rock type.

It is further known to determine the electrical resistivity of geologic formations surrounding and between boreholes drilled into the geologic formations of interest, with electromagnetic (EM) measurements from the surface, including the sea bottom, from surface-to-borehole, and/or between boreholes (crosswell EM).

In two articles, "Crosshole electromagnetic tomography: A new technology for oil field characterization", The Leading Edge, March 1995, by Wilt et al. and "Crosshole electromagnetic tomography: System design considerations and field results", Society of Exploration Geophysics, Vol. 60, No. 3, 1995 by Wilt et al., the authors describe the principles guiding the measurement of geologic formation resistivity with low frequency EM systems.

Methods and tools for performing EM measurements are further described in a number of patents and patent applications including the co-owned U.S. Pat. No. 6,393,363 to Wilt and Nichols.

In "Using Crosswell Electromagnetic to Map Water Saturation and Formation Structure at Lost Hills". SPE Western Regional Meeting, 26-30 Mar. 2001, Bakersfield, Calif. (SPE paper 68802) by M. Wilt et al., the authors describe a qualitative method of estimating the change in water saturation from time-lapse cross-well EM data.

The published international patent application WO2001/020366 provides further background related to reservoir resistivity mapping with deep electromagnetic measurement. It also teaches the combination or joint inversion of resistivity depth images with other geological and geophysical data to estimate the reservoir properties. The co-owned U.S. Pat. No. 7,363,164 to Little and LaVigne describes Archie and Waxman-Smits laws in the context of using dual and triple water models to interpret electrical resistivity measurements.

In view of the known art, it is seen as one object of the present invention to provide a new method of determining saturations, wettability or combined saturation and wettability maps covering the formation at a distance from the immediate vicinity of a borehole. More specifically, it is seen as an object of the invention to provide a method of extrapolating measurements into the space between two or more boreholes to determine saturations and/or wettability or related parameters at locations not accessible for direct measurements of such parameters.

SUMMARY OF INVENTION

According to a first aspect of the present invention, there is provided a method for assigning a saturation and wettability or related parameter to a subvolume of formation located between two or more boreholes, the method including the steps of obtaining measurements of the resistivity at the subvolume, obtaining further parameters determining a relation between resistivity and saturation from logging measurements along the two or more boreholes, obtaining geological measurement defining geological or rock-type boundaries within the formation between the two or more boreholes, selecting the subvolume such that it is intersected by the geological or rock-type boundaries; transforming the resistivity measurements into the saturation at the subvolume; and using the saturation and/or the further parameters to determine the wettability or related parameter for the subvolume.

The subvolume is best determined by using a combination of known logging measurements which provide layer bedding information and seismic measurement which provide stratigraphic and other geological information about the layer structure of the reservoir far away from boreholes, i.e., beyond the depth of investigation of the logging measurements.

The resistivity is preferably obtained from EM surveys, particularly cross-well EM surveys.

The relationship used to transform the resistivity into saturation values is preferably an Archie-type relation including known variants and equivalents.

In a variant of the invention, the coarser resolution of the measurements of the resistivity at the subvolume is refined using a dimensionless distribution of parameter values as obtained from logging measurements having a finer resolution at the borehole.

Further details, examples and aspects of the invention will be described below referring to the following drawings.

DETAILED DESCRIPTION

Figure 1:
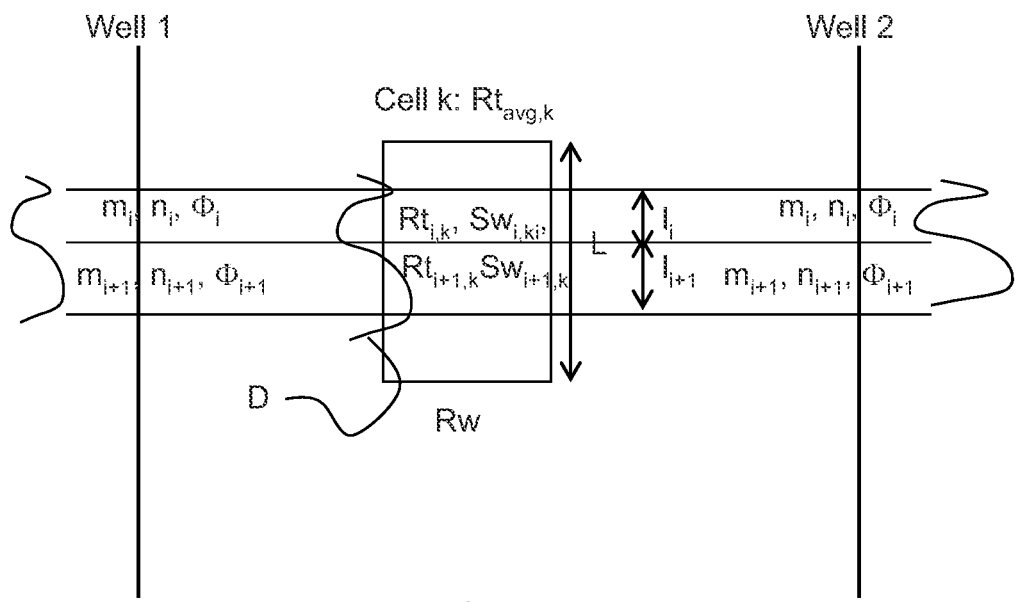
FIG. 1 illustrates the delineation, interpolation and resolution refinement of the present invention.

In the following, steps are described to derive local values of saturation, wettability and related parameters in the reservoir at locations far from a borehole. At such locations standard logging methods fail due to a lack of available depth of investigation. Even advanced logging methods are currently not suited to measure formation parameters beyond several meters from the borehole. Hence, it will be understood by a person skilled in the art that methods in accordance with the present invention apply to the measurement of formation parameters at locations at least 10 m away from a borehole.

For the present example a map of resistivity values Rt for a reservoir volume is determined or assumed to be determined. Such resistivity (or conductance) maps can be gained from crosswell, surface-to-borehole or other variants of electromagnetic (EM) surveys.

Crosswell EM uses the principles of electromagnetic induction and tomography to provide an image of the resistivity distribution between boreholes. An induction coil transmitter is placed in a first well and it broadcasts EM signals throughout the medium. In a second well, the signals are detected using an array of induction coil (magnetic field) receivers. The sources and receivers are placed at regularly spaced intervals below, within, and above the depth range of interest and the collected data are used to image the inter-well space. Indeed, the collected data has good sensitivity to the Eddy currents running in the medium whose magnitude depends on the formation resistivity.

Field data are interpreted by fitting the measurements to calculated data from a numerical model, using an inversion procedure. An inversion typically begins with a resistivity model as derived from prior knowledge of the field including logs, geologic and seismic data. A forward EM modeling method is applied to obtain the response from the initial model. The modeled data are then fitted to the measured data using often additional constraints and the best fit results in the inter-well mapping of resistivity. The constraints are required to improve the speed and results of the inversion. The process is applied between two lines of receivers and transmitters for a two-dimensional (2-D) resistivity mapping of the formation but can be extended to three or more non-aligned wells and to a 3-D inversion.

The crosswell EM measurement alone can rarely provide directly a saturation or wettability mapping of the reservoir as many parameters can influence and modify the apparent resistivity of the medium. Therefore, further parameters are introduced to serve as constraints to determine saturation or wettability.

Firstly, a delineation of geological structures such as layer boundaries or boundaries between different rock types is conducted. This can be performed at a reservoir scale using seismic measurements or at a borehole scale using logging measurements sensitive to changes of rock type and/or layer boundaries.

Using for example seismic profiles of the formation it is possible to delineate the various geological layers in the inter-well space where the EM measurement is carried out. This delineation provides a large scale definition of the predictable connection of the geological patterns between the discrete measurement points.

The precision of the seismic measurements are typically limited by the wave length of the seismic wave but it provides the local slopes and thus allows establishing a conformal transformation of the layers between the measurement wells.

Further, local measurements are used to determine the actual sequenced stratigraphic that are signature of the same geological pattern between these discreet points of measurements. The measurements can include core measurements from the different locations, formation images as acquired using borehole instruments such as the Formation Micro Imager (FMI) or other logging measurements or formation sampling instruments.

FMI images provide, for example, detailed images of the formation with an accuracy or resolution of about one centimeter, leading to an accurate knowledge of the formation bedding at this length scale. Preferably, core measurements may be used for extremely accurate determination of the micro-geologic patterns of each layer, and the geo-statistic variograms determining the variability of the wettability parameters in a geological stratification.

Once the layer and/or rock type structure is established, the formation around a borehole and between boreholes can be divided into subvolumes respecting these boundaries.

In addition to the delineation process, additional parameters are assigned to the subvolumes defined by the above process. Based for example on the hypothesis that a given geological layer has produced a similar rock structure and fluid/rocks interaction for similar fluids in the range of the cross well electromagnetic measurement, many parameters as measured in one or more wells can be extrapolated or interpolated to assign parameter values to the subvolumes of the formation between the wells. This assumption can be verified, calibrated and/or modified using measurements made on cores locally extracted from each well. The patterns do not have to match exactly across different wells but provided they are similar, an interpolation can be conducted to populate the inter-well space with parameter values.

Among the many quantities that can be interpolated are wettability as defined for example by contact angle or by wettability NMR index, Amott-Harvey index, USBM index as measured on cores, wireline log data, NMR data, directly or indirectly linked to the wettability index as described for example by U.S. Pat. No. 6,765,380 to R. Friedman and M. D. Hurlimann as well as by Looyestijn, W. and J. Hofman, Wettability-Index Determination by Nuclear Magnetic Resonance, Journal of the Reservoir Evaluation & Engineering, 9(2) 2006, 146-153. Others parameters which can be interpolated are relative permeability curves or capillary pressure curves, all of which can be approximated using known methods based on core or logging measurements.

For the following quantities such as the cementation and saturation exponents m and n as found in Archie-type relations, and porosity $\Phi$ are introduced and assumed to follow a similar pattern along the two or more wells surveyed by cross-well EM. Methods to determine these parameters are well established using for example core tests and various logging tools and measurements. For instance the cementation factor m can be determined by the process explained in the published United States Patent Application 2009/0259403; and a direct estimate of m and n can also be gained from dielectric measurements in the bore hole. The value of the resistivity of the water in the formation (Rw) can be measured at the well location by either interpretation of resistivity logs (Wireline or D&M) in a water zone; down-hole sample (MDT); or surface sampling.

Once the quantities m, n, Rw and $\Phi$ are measured or derived at the wellbores location, they are then interpolated to populate the inter-well space in order to yield an apparent water saturation map by incorporating inter-well resistivity and using an Archie-type relationship as described in more detail below. The Archie-type relations define a relation between the resistivity and the saturation of the medium, using the porosity and saturation and cementation exponents m and n. It is usually assumed that these parameters do not vary significantly along a geological layer. Knowledge of the fluid composition of the formation is also supposed to be available.

If all parameters are known for each layer the up-scaling and mapping at the reservoir level becomes possible if the medium between the control wells is reasonably homogeneous. It is always possible that some parts of the reservoir are not connected geologically and calibration of the set of parameters n, Rw, m, $\Phi$ is not possible at every part of the formation. This is of course a limitation for any up-scaling scheme.

A water saturation map can only rigorously be derived using the poorest resolution of all the inputs, which is expected to be the one of the resistivity, which is about 5 m vertical resolution for a cross-well EM survey. However the detailed description below shows how if sequence stratigraphy exhibits fine geological layering with a reproducible pattern from well to well and if the quantities of interest such as n, m and porosity can be evaluated for each layer at each well, a finer map of water saturation can be estimated. This process is illustrated using FIG. 1.

For properties derived from crosswell measurements ($R_t$, $S_w$, I . . . ) a normalization is performed by the average value taken at the cell resolution leading to a non-dimensional distribution D of these properties in each cell. Then the interpolating process is carried out on these averaged values and the finer description can be obtained in each cell k by imposing the non-dimensional distribution D of these properties to be the same along each layer (e.g. as marked by the index i in FIG. 1). The effective amplitude of the distribution D being provided by the EM measurement at larger scale in the same vicinity.

In the example of FIG. 1, the quantities m, n and $\Phi$ are constant or show very little variation in each layer, while the resistivity of the water phase is assumed constant in the inter-well space. Inversion of cross-well EM measurement yields one resistivity value $Rt_{avg}$ per grid cell of thickness L (L≈5 m) as determined by the resolution of the EM survey. At the k-th cell position shown in the center of FIG. 1, this observable is linked to the resistivity within each layer by the relationship:

$$\sum_i \frac{l_i}{Rt_{i,k}} = \frac{L}{Rt_{avg,k}}. \qquad [3]$$

Figure 2:
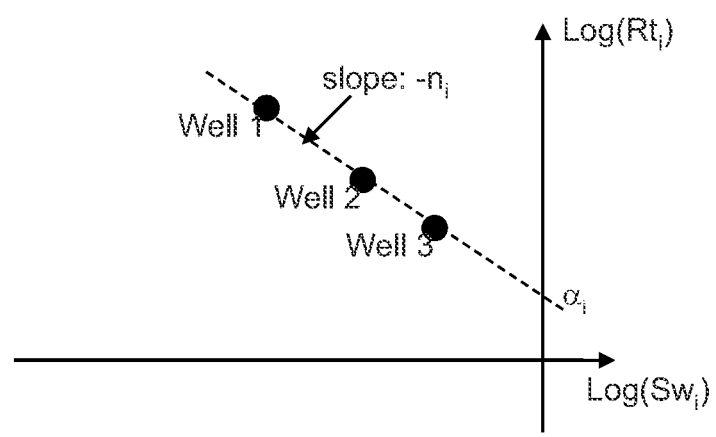
FIG. 2 is a plot linking parameters from several wells.

Resistivity can be measured at the wells. The resistivity value at the wells position differs from within the inter-well space due to saturation variation. The Archie relationship holds for the i-th layer:

$$\log(Rt_i) = \alpha_i - n_i \log(Sw_i) \qquad [4]$$

with the constant $\alpha_i = \log(Rw) - m_i \log(\phi_i)$. As shown in FIG. 2, known measurements demonstrate that this relationship holds between multiple wells within the same reservoir.

When using the value of the observable $Rt_{avg,k}$ from inversion of cross-well EM data in the k-th cell, the saturations in every layer intersecting the cell $Sw_{i,k}$ can be computed using this relationship.

The cross-well electromagnetic data provide apparent resistivity of the formation between the various measurement wells. It is however challenging to directly transform these data in saturation data. The constraints imposed by continuation of local measurements as described in the previous section afford more confidence in this transformation between apparent resistivity and water (oil or gas saturation) between the wells.

In Neperian Logarithm, an Archie-type Law can be expressed for example as $$n \log(S_w) = \log(R_w) - \log(R_t) - m \log(\phi). \qquad [5]$$

The cross-well electromagnetic measurement only provides Log(Rt) and hence all the other parameters have to be up-scaled. It is obvious that a wettability mapping following the mapping of Log(Rt), requires the mapping of n and the geological knowledge of m, but it also requires that F is extrapolated everywhere in the reservoir. All these attributes are therefore imposed by local calibration at the well location, as described before.

Note that the knowledge of Log(Rw) (depending on the knowledge of the water in the rocks). If for instance the water is imported for flooding and pushing oil, the characteristics of the water and its history of motion of the reservoir must be recorded and integrated in the constraint model.

The above equation [5] can be refined by iteratively matching the saturation Sw and the saturation exponent n. In this variant the exponent n may depend on water saturation and on wettability angle or the wettability index I, i.e., n=n(Sw,l) or n=n($\theta$) see Donaldson, E. C., Siddiqui, T. K., Relation between the Archie saturation exponent and wettability, SPEFE, September 1989, 359-62. The iteration uses a starting value of n=$n_0$, which can be taken as the saturation exponent as assigned to the layer in which the cell is located and uses a modified Archie-type equation:

$$\text{Log}(S_{w0}) = \frac{1}{n_0}(\text{Log}(R_w) - \text{Log}(R_t) - m\text{Log}(\phi)). \quad [5A]$$

The above equation provides a saturation value $S_{w0}$. Using a relationship between saturations and wettability as described for example by Morrow, N. R., Capillary pressure correlations for uniformly wetted porous media. J. Can. Petroleum Technol. 15(4) 1975., pp. 49-69 and between wettability and saturation exponents as established for example by Donaldson and Siddiqui cited above, a new wettability and a new saturation exponent $n_1$ can be derived. Using the new $n_1$ for $n_0$ in eq. [5A] a second estimate $S_{w1}$ of the saturation is derived. Using a convergence criteria such as $|S_{wi} - S_{w(i+1)}| < \in$, ($\in$ being an arbitrary small convergence parameter) the iteration is stopped after the i+1 iteration and the final results $n_i$ and $S_{wi}$ for saturation exponent and saturation as well as for wettability are assigned as the accepted values for the grid cell under investigation.

Other models similar to the Archie model above predict a direct relationship between the resistance ratio (Rt/Rw) and the saturation Sw. As these relationships depend on the saturation exponent n, a fit of the measured data can be matched with curves as measured on cores on same lithology layers to again derive the saturation exponent n. This exponent can in turn be related to a wettability index or contact angle using the steps described above in reverse order.

It should be noted that this variant can be based solely on experimental data such as published by Sweeney, S. A. and Jennings, H. Y, The Electrical Resistivity of Preferentially Water-Wet and Preferentially Oil-Wet Carbonate Rock, Producers Monthly 24 (7): 1960 4 without pre-supposing a mathematically defined relationship between $S_w$, $R_t$, $R_w$ and n. In this case the wettability can be extracted from the empirical links between n and wettability indices as found on the cores extracted in the same bed, or by any other local direct measurements of wettability in wells (for instance with NMR).

Figure 3:
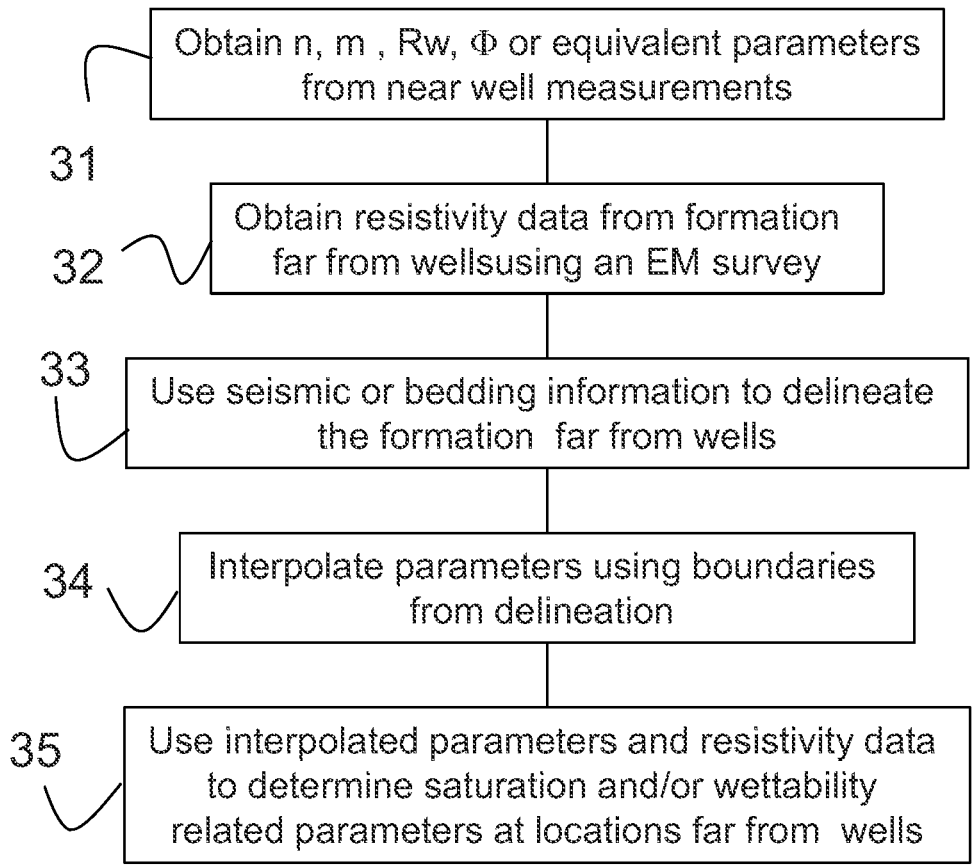
FIG. 3 is a flowchart of steps in accordance with an example of the invention.

The flowchart of FIG. 3 summarizes the steps described in detail above, including the Step 31 of obtaining n, m, $R_w$, $\Phi$ or equivalent parameters from near well measurements, the Step 32 of obtaining resistivity data from formation far from wells using an EM survey, the Step 33 of using seismic or bedding information to delineate the formation far from wells, the Step 34 of interpolating parameters using boundaries from the delineation step, and the Step 35 of using interpolated parameters and resistivity data to determine saturation and/or wettability related parameters at locations far from wells Moreover, while the preferred embodiments are described in connection with various illustrative processes, one skilled in the art will recognize that the system may be embodied using a variety of specific procedures and equipment and could be performed to evaluate widely different types of applications and associated geological intervals. Accordingly, the invention should not be viewed as limited except by the scope of the appended claims.

What is claimed is:

1. A computer-implemented method for assigning a saturation and wettability or related parameter to a subvolume of formation located between two or more boreholes, said method comprising the steps of:
    using an EM survey to obtain measurements of resistivity at said subvolume;
    obtaining further parameters determining a relation between resistivity and saturation from logging measurements from a logging tool along said two or more boreholes;
    obtaining a geological measurement defining geological or rock-type boundaries within said formation between said two or more boreholes;
    selecting said subvolume such that it is intersected by said geological or rock-type boundaries;
    transforming said resistivity measurements into said saturation at said subvolume wherein the step of transforming the resistivity measurements into the saturation at the subvolume includes extra- or intrapolating parameters measured at one or more wellbores to the location of said subvolume using knowledge of the layer boundaries in the formation; and
    using said saturation and/or said further parameters to determine said wettability or related parameter for said subvolume.

2. The method of claim 1, wherein the measurements of the resistivity include cross-well electro-magnetic or surface-wellbore electro-magnetic measurements.

3. The method of claim 1, wherein the further parameters are selected from a group consisting of a parameter related to porosity of the formation, a resistivity associated with the water in the subvolume, an exponent of said parameter related to porosity in the relation and/or an exponent of the saturation in said relation.

4. The method of claim 3, wherein in the determination of the saturation and the wettability the dependence of a saturation exponent on wettability is used.

5. The method of claim 1, wherein in the determination of the saturation and the wettability the dependence of a resistance ratio on said saturation is used.

6. The method of claim 1, wherein the further parameters include a parameter related to porosity of the formation and/or at least one of the Archie exponents.

7. The method of claim 1, wherein the geological measurement defining geological or rock-type boundaries are seismic measurements.

8. The method of claim 1, wherein the geological measurement defining geological or rock-type boundaries are sonic and ultrasonic, resistivity, nuclear, dielectric, optical or other logging measurements capable of identifying layer boundaries or other discontinuities along the wall of a wellbore.

9. The method of claim 1, wherein the step of transforming the resistivity measurements into the saturation at the subvolume includes extra- or intrapolating parameters measured at one or more wellbores to the location of said subvolume using knowledge of the layer boundaries in the formation and a distribution of said parameters at a scale smaller than a resolution of the resistivity measurement to determine the saturation and/or wettability related parameters at a resolution exceeding said resolution of said resistivity measurement.

* * * * *